(12) United States Patent
Cozean et al.

(10) Patent No.: US 6,764,309 B2
(45) Date of Patent: Jul. 20, 2004

(54) METHOD AND LASER APPARATUS FOR PREVENTING TOOTH DECAY

(75) Inventors: Colette Cozean, Lake Forest, CA (US); Lynn Powell, Salt Lake City, UT (US); Samir Nammour, Brussels (BE)

(73) Assignee: Nocari, LLC, Lake Forest, CA (US)

( * ) Notice: Subject to any disclaimer, the term of this patent is extended or adjusted under 35 U.S.C. 154(b) by 0 days.

(21) Appl. No.: 10/093,957

(22) Filed: Mar. 6, 2002

(65) Prior Publication Data

US 2003/0170586 A1 Sep. 11, 2003

(51) Int. Cl.$^7$ ............................. A61C 5/00; A61K 6/00

(52) U.S. Cl. .......................................... 433/215; 433/29

(58) Field of Search ........................... 433/29, 215, 216

(56) References Cited

U.S. PATENT DOCUMENTS

| | | | |
|---|---|---|---|
| 4,273,535 A | * 6/1981 | Yamamoto et al. | 433/215 |
| 4,732,617 A | 3/1988 | Causton et al. | 106/35 |
| 4,877,401 A | 10/1989 | Higuchi et al. | 433/215 |
| 5,145,667 A | 9/1992 | Ibrahim et al. | 424/52 |
| 5,616,141 A | 4/1997 | Cipolla | 606/15 |
| 6,026,828 A | * 2/2000 | Altshuler | 433/29 |
| 6,102,696 A | 8/2000 | Osterwalder et al. | |
| 6,439,888 B1 | * 8/2002 | Boutoussov et al. | 433/215 |

FOREIGN PATENT DOCUMENTS

| | | |
|---|---|---|
| DE | 100 09 004 A | 10/2001 |
| EP | 0 743 029 A | 11/1996 |
| WO | WO 98 58595 A | 12/1998 |
| WO | WO 00 67048 A | 11/2000 |

OTHER PUBLICATIONS

"Caries–like Lesion Initiation and Progression Around Laser–cured Sealants" by M. John Hicks, DDS, MS, PhD, MD et al., AM. J. of Denistry, vol. 6, No. 4, Aug. 1993, pp. 176–179.

"Comparison of Three Lasers on Demineralization of Human Enamel" by G. Lynn Powell et al., SPIE vol. 1880, pp. 188–192.

The Effects of Argon Laser Irradiation on the Initiation and Progression of Enamel Caries: An in–vitro Study by Richard J. Blankenau, DDS et al., C U Dental, Nov. 10, 1997, 4 pages.

"Enhancement of Argon Laser Effect of Dissolution and Loss of Human Enamel" by Duncan Yu, Ph.D. et al., J of Clinical Laser Medicine & Surgery, vol. 11, No. 5, 1993, pp. 259–261.

"Caries–like Lesion Initiation and Progression in Sound Enamel Following Argon Laser Irradiation: An in–vitro study" by M. John Hicks, DDS, MS, Ph.D, MD et al., Journal of Dentistry for Children, May–Jun. 1993, pp. 201–206.

"Root Caries In Vitro After Low Fluence Argon Laser and Fluoride Treatment" by M. John Hicks, DDS, MS, PhD, MD et al., Compendium, Jun. 1997, pp. 543–552.

(List continued on next page.)

Primary Examiner—Cary E. O'Connor
(74) Attorney, Agent, or Firm—Knobbe, Martens, Olson & Bear, LLP

(57) ABSTRACT

A method and apparatus for preventing tooth decay by treating the tooth surface, including the occlusal surface and unexposed surfaces such as subgingival, interproximal, and contact areas, with a laser with a coherent or noncoherent light source are described. This process makes the tooth more resistant to acid and better able to bond fluoride, thus requiring a lower concentration of fluoride. The method allows the treatment to penetrate deeper into the tooth then previously accomplished with other methods and can be used in a dental office or at home.

26 Claims, 5 Drawing Sheets

OTHER PUBLICATIONS

"In Vivo Caries–Like Lesion Prevention with Argon Laser: Pilot Study" by Richard J. Blankenau, DDS et al., J of Clinical Laser Medicine & Surgery, vol. 17, No. 6, 1999, pp. 241–243.

"Argon Laser Irradiation in Root Surface Caries: in vitro Study Examines Laser's Effects" by Gary H. Westerman, DDS, MS et al., JADA, vol. 125, Apr. 1994, pp. 401–407.

"Combined Effects of Acidulated Phosphate Fluoride and Argon Laser on Sound Root Surface Morphology: An in vitro Scanning Electron Microscopy Study" by Gary H. Westerman, DDS, MS et al., J of Clinical Laser Medicine & Surgery, vol. 17, No. 2, 1999, pp. 63–68.

"The Combined Effects of Laser Irradiation and Chemical Inhibitors on the Dissolution of Dental Enamel" by Jeffrey L. Fox et al., Department of Pharmaceutics, University of Utah.

"Effects of argon laser irradiation and acidulated phosphate fluoride on root caries" by M. John Hicks, DDS et at., American Journal of Dentistry, 1995, vol. 8, No. 1, Feb., pp. 10–13.

"Argon laser irradiation and acidulated phosphate fluoride treatment in caries–like lesion formation in enamel: an in vitro study" by Catherine M. Flaitz, DDS, MS et al., American Academy of Pediatric Dentistry, 1995, vol. 17, No. 1, pp. 31–35.

"Argon laser effect on demineralization of human enamel" by G. Lynn Powell, Laser Surgery, 1992, vol. 1643, pp. 374–379.

"Combined effects of argon laser irradiation and fluoride treatments in prevention of caries–like lesion formation in enamel: an *in vitro* study" by Syed M. Haider et al., The Journal of Clinical Pediatric Dentistry, 1999, vol. 23, No. 3, pp. 247–256.

"Effects of Laser Irradiation on Occlusal Surfaces of Human Molars." By R.L. Slayton and J.S. Wepel, 1991 IADR Abstract, No. 1818.

"Treating Occlusal Pit and Fissure Surfaces by IR Laser Irradiation" by Douglas A. Young, Daniel Fried, and John D.B. Featherstone. SPIE vol. 3810 (2000).

"Nd: YAG Laser in Caries Prevention: a Clinical Study" by D.M. Zezell, H.G.D. Boari, C.P. Eduardo. Abstract and Presentation from $1^{st}$ Congress—European Society for Oral Laser Applications, Vienna, Austria. May 17–20, 2001.

Proceedings of "Third International Congress on Lasers in Dentistry", pp. 41–42, Salt Lake City, Utah. August 6–8, 1992.

* cited by examiner

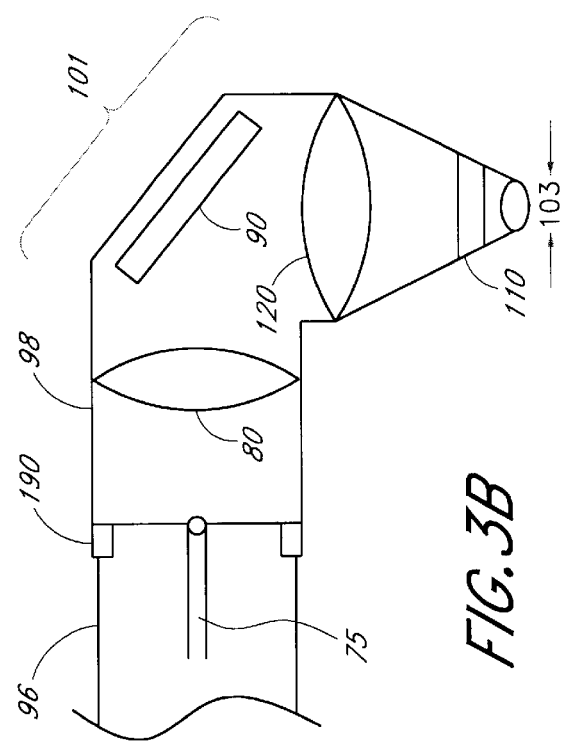
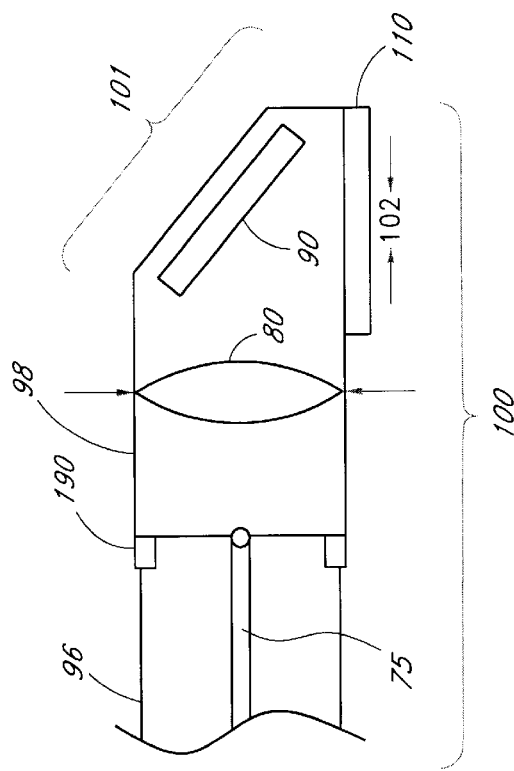
FIG.3B
FIG.3A

METHOD AND LASER APPARATUS FOR PREVENTING TOOTH DECAY

FIELD OF THE INVENTION

This invention relates to an apparatus and a method for preventing tooth decay using electromagnetic radiation.

BACKGROUND OF THE INVENTION

Tooth decay is caused by demineralization of the tooth structure at either the enamel or root surface. The enamel is a thin layer (1–2 mm) composed of a crystal-type structure of hydroxyapatite or calcium phosphate hydroxide, containing large amounts of calcium and phosphorus. Dental enamel is a porous material and although it contains about 96% by weight of mineral, this is equivalent to approximately 85 percent by volume. The remaining 15 percent by volume is made up of water, protein and lipid, which form the diffusion channels through which acids and minerals can travel into or out of the tooth. The dentin, the major part of the core of the tooth, is composed of $CaCO_3$, a chalk-like material. Although it is 70% by weight of mineral, it also contains 20% by weight organic and 10% by weight water. This corresponds to 47% by volume mineral.

Tooth decay, or dental caries results from the growth of bacteria on the tooth. The bacteria metabolize sugars to acid which can dissolve the tooth. The bacteria grow as a plaque on the tooth and conventional treatment involves periodic removal of the plaque and strengthening of the tooth to make it more resistant to the acid produced by the bacteria.

The majority of tooth decay occurs in the occlusal and unexposed surfaces of the tooth. The tooth is composed of the lingual (back), buccal (front), and occlusal (top) surfaces. The lingual and buccal surfaces are considered to be "flat" although there are grooves and fissures. The occlusal surface is very uneven, composed of pits, fissures, and protuberances. Because of the way the teeth are formed in the mouth, there are also unexposed surfaces of the tooth, such as subgingival surfaces, interproximal surfaces, and contact surfaces.

Methods to prevent tooth decay have typically concentrated on the buccal and lingual surfaces. Unexposed surfaces are usually not treated. Sealants are consistently used on the occlusal surfaces because other methods are relatively ineffective on the occlusal surfaces due to the very different structure and composition of the occlusal surface. The differences include a harder and more fissured surface, the enamel is generally thicker and the structure possesses a different angulation of prisms. In addition, fluoride has previously been shown to be ineffective on the occlusal surface.

Common professional methods to prevent tooth decay have included fluoride, pit and fissure sealants, and varnishes. However, none of these methods individually protect all of the tooth surfaces nor are they permanent, usually lasting less than 5 years. In addition, heat treatment has been explored as an alternative method. By treating the tooth with a very high heat, from 250–1000° C., the structure of the tooth is changed, making it more resistant to acid. This method has never been used clinically because of safety concerns. Because most of the changes to the tooth occur at a very high heat, 1200° C., some changes occur between 500° C. and 1000° C. and a few were seen at temperatures as low as 250° C. to 400° C., there is the potential for thermal damage to the underlying pulpal tissue, adjacent soft tissue and osseous structures. Therefore, although the effects of laser irradiation on dental caries and tooth structure were explored some 30 years ago, the risk of thermal damage to the adjacent hard tissue and pulp was such that much of the research was abandoned. Several laser wavelengths have been explored, including $CO_2$ and Nd:YAG, but both produce a significant amount of heat on the surface of the tooth and in the pulp and provide only a shallow treatment of the tooth itself. With improved laser technology, a number of different types of lasers with varying tissue penetration and energy levels have been developed.

The structural changes produced during the application of heat by $CO_2$ and Nd:YAG lasers at these very high heats include a change in the phosphate molecule in the hydroxyapatite. This makes the tooth less soluble and increases resistance to decay. However, the level of heat produced by these lasers has not been used clinically because it has been shown to damage the tooth structure itself as well as potentially damaging soft tissue.

The action of the laser, as well as other types of tooth treatments, to produce resistance of the tooth to acid can be envisioned as follows: it has been hypothesized that tooth enamel crystals ("hydroxyapatite") possess two types of sites from which dissolution can occur. The first type of site (the "thermal" site) is less resistant to dissolution by acids under conditions typically found in the oral environment than is the second type of site (the "chemical" site). The treatment of tooth enamel by carbon dioxide laser irradiation or by high temperatures eliminates or reduces the thermal sites, leaving only the chemical sites for dissolution to occur. Once the thermal sites have been eliminated, the tooth enamel is then treated to eliminate the chemical sites with dissolution rate inhibitors or chemical agents. However, even if such laser treatments were clinically usable for safety reasons, they have the disadvantage that they produce only a surface treatment and cannot protect all of the tooth structure, particularly the occlusal and unexposed surfaces.

Therefore, all of these methods are rendered undesirable by that fact that they can only provide temporary treatment, act only at a very shallow depth of the tooth at the lingual and buccal surfaces, and some cannot be used due to safety issues. In addition, none of the above methods can be used in a non-professional setting.

SUMMARY OF THE INVENTION

One aspect of the invention is a method of treating a living tooth in a mammal's mouth, comprising irradiating the unexposed and occlusal surfaces of said tooth with light having a wavelength in the range of between from about 400 nm to about 810 nm, and an energy and an energy density sufficient to vaporize water and organic material without damaging the pulp of the tooth. In one embodiment, the treatment heats the localized sites to a temperature of no more than about 250° C. In a further embodiment, the treatment heats the localized sites to a temperature of no more than about 200° C. In a further embodiment, the treatment heats the localized sites to a temperature of no more than about 100° C. In a further embodiment, the treatment heats the localized sites to a temperature of no more than about 50° C. In one embodiment, the unexposed surfaces are the subgingival, interproximal, and contact areas of the tooth.

Preferably, the vaporization of organic material and water occurs from 3 microns to 50 microns beneath the surface of the tooth. The energy density may be between about 5 $J/cm^2$ to 65 $J/cm^2$, preferably about 5 $J/cm^2$ to 30 $J/cm^2$, and more preferably between about 5 $J/cm^2$ to 12 $J/cm^2$.

In one embodiment, the method further includes bonding a chemical agent to the crystalline structures of the tooth after removal of the organic compound.

In one embodiment, the light beam is a coherent light source, such as a laser, preferably an argon laser or a diode laser. In one embodiment, the argon laser beam is applied at 250 mW. In a further embodiment, the light beam is an incoherent light source, preferably an LED.

In one embodiment, the chemical agent is fluoride, including an effective concentration of fluoride is less than or equal to 200 ppm of stannous fluoride (0.08%) or 1000 ppm of sodium fluoride (0.275%). Typically the fluoride acts by binding to hydroxide groups within the hydroxyapatite crystal.

In one embodiment, the laser is applied for 10 seconds for each treated surface. Alternatively the tooth is treated for a period of time of more than 1 sec for each treated surface.

A further aspect of the invention is an apparatus for the treatment of a tooth, comprising a handpiece and a light source having a wavelength in the range of between from about 400 nm to about 810 nm. In one embodiment, the light is output transverse to the longitudinal axis of the handpiece. The handpiece is adapted to provide at least two spot sizes for the output beam. Preferably, this is accomplished by providing interchangeable tips, one of which provides a relatively large spot size for treating lingual and buccal surfaces, and the other of which provides a relatively small spot size for treating at least interproximal surfaces.

In one embodiment, a method of treating between teeth is disclosed, which includes irradiating said tooth surface with a laser. In a further embodiment, the method further comprises applying fluoride to a tooth surface, including the occlusal and unexposed surfaces prior to or after irradiation.

BRIEF DESCRIPTION OF THE DRAWINGS

In FIG. 2A the diameter of the resulting beam is 8 mm.

FIGS. 3A and B are side views of an embodiment of the laser handpiece in which the tip is exchangeable. In FIG. 3A the diameter of the resulting beam is wide. In FIG. 3B the diameter of the resulting beam is narrow.

In FIG. 5A the diameter of the resulting beam is wide.

DETAILED DESCRIPTION OF THE PREFERRED EMBODIMENT

Figure 1A:
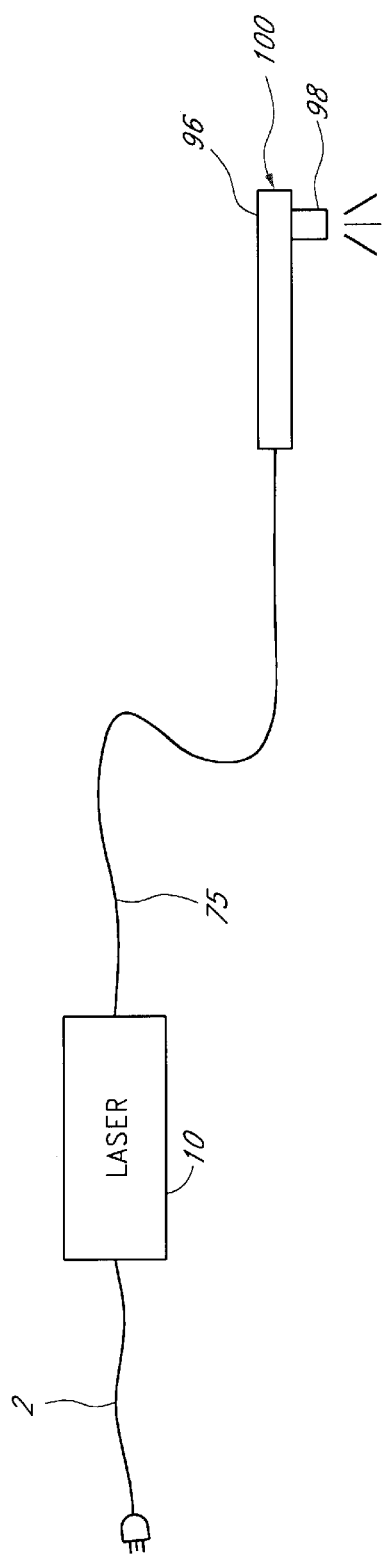
FIG. 1 is a side view of a preferred embodiment of the laser handpiece of the invention.

A preferred method and apparatus are disclosed herein which change the solubility of the surfaces of a tooth without significant production of heat, typically using temperatures of less than 200° C. and even as low as 50° C. The method and apparatus allow for a deeper treatment of the tooth, as well as the use of a lower concentration of fluoride, and have the potential to allow one to keep teeth completely free of caries for the lifetime of the patient. The preferred embodiment advantageously allows for the treatment of all surfaces of the tooth, including the occlusal surface as well as the unexposed surfaces of the tooth. The preferred method uses a visible light beam alone or in combination with a chemical agent to prevent dental caries. Surprisingly, while the action of a visible light beam and the action of fluoride both act separately to increase resistance of the tooth to decay, the action of the two together is not additive, but synergistic.

While not limiting the scope to any particular theory or mechanism of action, the following theoretical considerations may explain the synergistic combination which is observed in the practice of this method. Certain of the theories and information about fluoride may be additionally found in Higuchi, et al. U.S. Pat. No. 4,877,401, incorporated herein by reference.

The application to the tooth of light from a suitable light source (i.e. an argon laser) at low power acts on the "thermal sites" or localized sites which contain concentrations of water and/or organic material beneath and in proximity to the surface of the tooth. This results in a much reduced temperature (usually around 100° C.) which produces considerably less heat than $CO_2$ or comparable lasers. The visible light beam reduces the carbonated phase of the hydroxyapatite, making the tooth more resistant to attack. The removal or vaporization of carbonate lowers the solubility and changes the water content of the hydroxyapatite. It also changes the phase of the hydroxyapatite and makes it more pure. There is a reduction in the size of the hydroxyapatite crystal as well as an increased hardness in the tooth structure. The treatment may remove water from the structure of the tooth, providing an ion imbalance which attracts fluoride. All of these changes result in the increased capability of the tooth to resist demineralization, a precursor to tooth decay.

Fluoridation, or other chemical agents act on the "chemical sites" by binding to hydroxide radicals and sterically or chemically preventing the action of acid on those sites. However, fluoride can accumulate in the body and too much fluoride can result in fluorosis, a syndrome whereby teeth are discolored, resulting in white splotchy areas on the enamel during development which may be accompanied by other symptoms. Children are particularly susceptible to fluorosis and can obtain too much fluoride simply from tap water and toothpaste which is accidentally swallowed during brushing. In addition, more serious diseases have been linked to too much fluoride including iodine deficiency disorders, confusion, drowsiness, and listlessness. Advantageously, it was found that the above-mentioned laser treatment results in a situation in which less fluoride is necessary to provide a protective result, thus reducing the incidence of fluorosis. Without being limited to a particular theory, it is thought that because of a shrinkage of the hydroxyapatite crystal during laser treatment, there are fewer "chemical" sites exposed and thus, less fluoride is necessary to provide the same protection.

Although the light source of the preferred embodiment produces coherent light, sources that produce incoherent light may also be used. The sources should be selected to increase the acid resistivity of tooth enamel at low power (producing less heat). Preferably, the source emits one or more wavelengths which are not absorbed by water, but are absorbed by organic compounds. Preferably, the wavelengths are between about 400 and 810 nm, more preferably between about 457 and 514 nm, such as produced by an argon gas laser. Solid date lasers, diode lasers, and light emitting diodes (LEDs) that emit light within the 400–810 nm range may also be used. In one embodiment, the argon laser is used into the green region of 512 nm.

The light sources need only be used at low power to produce the desired effect. For argon lasers, the applied light beam may have an energy density below about 65 J/cm$^2$, preferably about 30 J/cm$^2$, preferably an energy density below about 12 J/cm$^2$ and in some cases may be used below about 6 J/cm$^2$.

Preferably, a chemical agent, such as fluoride, is applied to the tooth surface in connection with treatment by the light beam. For example, the fluoride can be applied as a paste before treatment with the laser or after treatment with the laser. Alternatively, the fluoride can be applied as a mouthwash or as part of a toothpaste. The fluoride may also be applied as a patch, providing a low concentration of fluoride in a timed-release manner. For example, mucoadhesive fluoride tablets consisting of a bioerodible matrix which dissolves completely after depletion can be used such as those described in Bottenberg et al. J Dent. Res. 77(1): 68–72. Treatment with the light beam allows the fluoride to penetrate 50–100 microns beneath the surface of the tooth.

Fluoride (Fl—) interacts at several stages of the caries process to inhibit progression or enhance reversal. The following three mechanisms of action are now considered to be the most important way in which fluoride works. First, fluoride has antibacterial properties at lower pH in the plaque when it enters the bacterial cell as HFl. When fluoride enters the bacteria it interferes with the enzymes inside the bacteria, slowing down or inhibiting acid production. Second, when fluoride is present in the aqueous phase on and within the tooth at the same time as an acid challenge, it dramatically inhibits dissolution of calcium and phosphate at the crystal surfaces in the subsurface regions of enamel. If fluoride is present in the tooth crystals where it is incorporated systematically during tooth development, it will dissolve out during the demineralization process and help to inhibit subsequent demineralization. Lastly, fluoride present in the aqueous phase at the crystal surfaces within the tooth speeds up the recrystallization by helping to bring calcium and phosphate ions together. This provides a much more acid-resistant "new" crystal surface. During subsequent acid challenges following ingestion of fermentable carbohydrates the acid bypasses this resistant mineral, and is forced to go deeper into the tooth before mineral can be dissolved making decay less and less likely to progress. Remineralization following demineralization in this way makes the tooth more and more resistant as time progresses with these natural pH-cycles. Examples of other suitable chemical agents include: ethane-1-hydroxy-1,1-diphosphonic acid, and dodecylamine HCl. The fluoride (or other chemical) composition may be any mouthwash, toothpaste, gel, restorative material, paste, patch, etc. that uses existing or lower concentrations of fluoride in association with laser treatment. The restorative material may be placed on the tooth and cured with a laser. It has been shown herein that the restorative material may contain lower concentrations of fluoride and still be equally effective.

In the method disclosed herein, the aforementioned change to the tooth surface caused by treatment with light may occur at 250° C., at 200° C., and may occur as low as 100° C. or even 40° C., because the organic material vaporizes at about 100° C. or in some cases as low as 40° C. Thus, the changes may occur at 110° C., 120° C., 130° C., 140° C., 150° C., 160° C., 170° C., 180° C., 190° C., 210° C., 220° C., 230 C., and 240° C. However, in some embodiments, the changes may occur as low as 50° C., including 60° C., 70° C., 80° C., 90° C. and the method may work at lower temperatures, including 40° C.

As mentioned, the teeth may be treated with fluoride before or after lasing. The fluoride may be left prior to lasing or the tooth may be lased immediately after application of the fluoride. Alternatively, fluoride may not be added at all.

The light beam may be used at a spot size of from about 5 to about 8 mm, including 5.5 mm, 6 mm, 6.5 mm, 7 mm, and 7.5 mm. However, it is advantageous to be able to vary the spot size so that smaller spot sizes may be used to treat smaller areas. Smaller spot sizes may range from about 1 mm to about 4 mm, including 1.5 mm, 2 mm, 2.5 mm, 3 mm, and 3.5 mm. Preferably, the spot size is larger for the flatter lingual and buccal surfaces and smaller for the occlusal and interproximal surfaces.

In one embodiment, a variety of exchangeable tips that produce different spot sizes may be attached to the handpiece. Tips producing the larger spot sizes would be used to treat the flatter areas of the tooth and the tips producing the smaller spot sizes would be used to treat the areas of the tooth which are more difficult to reach as well as the more uneven areas of the tooth such as the occlusal surfaces.

Through use of the preferred wavelengths, the treatment of the tooth with light vaporizes water and organic material to a depth of up to 50 microns to 2500 microns beneath the surface of the tooth, without thermal damage to the tooth structure. The light may also be used to treat subgingival tooth surfaces covered by thin (i.e., less than 200 or 300 microns) gum tissue. The light penetrates through the thin layer of gum into the tooth. In addition, the laser may be effectively used to treat crevices, contact areas, and interproximal areas. For example, light may be directed between a pair of adjacent teeth that are contacting each other. The direction of the light beam would be parallel to the contact surfaces. The beam is able to penetrate several (e.g., 2–3) millimeters into the tooth so that in some cases the beam will pass completely through the area where the surfaces are in contact. Accordingly, the preferred methods are useful not only for exposed easily accessible surfaces, but can be used to treat virtually every surface of the tooth, including unexposed surfaces.

The preferred embodiments of the laser handpiece for use with the methods disclosed herein will now be described with reference to the figures. As shown in FIG. 1, an optical fiber 75 is connected to transmit light from a light source 10 to a dental handpiece 100. Preferably, the light source is a conventional argon gas laser. The optical fiber has a core, a cladding and a protective jacket. The core preferably consists of glass (quartz or fused silicon) and has a diameter of 400 to 600 microns. The cladding may be of the same material as the core, but doped to provide a lower index of refraction. The jacket may be of plastic. The dental handpiece may be ergonomically similar to conventional handpieces used by dental professionals. Thus, the dental handpiece is envisioned to be small, lightweight and easy to use. Typically, the dental handpiece will have a switch for activating the laser 10, and the laser 10 will preferably be powered by A.C. through an electrical cable 2.

Figure 1B:
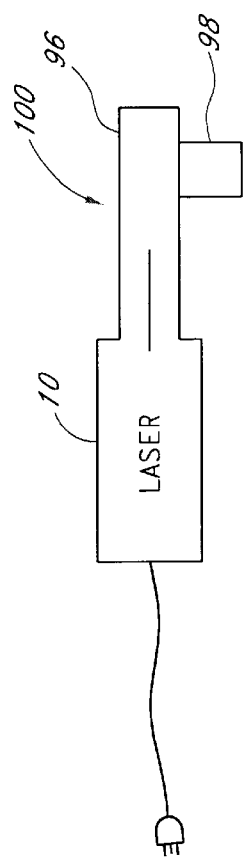

In another embodiment, shown in FIG. 1B, the laser 10, fiber optic 75, and dental handpiece 100 are integrated into a single hand-held unit. It is envisioned that in this case, in order to provide an apparatus which is small and light enough to be held, the light source may be a small diode laser which emits, for example, at from 468 to 810 nm. In addition, the energy source may be A.C. power supplied through a cable or batteries that are integrated into the hand-held unit.

The handpiece (FIG. 1A) or the housing of the hand-held unit (FIG. 1B) may be configured in any way known to one of skill in the art, particularly with a shape that allows it to be easily held. In addition, the handpiece or housing may include any type of material which allows it to be more easily gripped, including a rubber grip. The handpiece or housing may be indented in the area which will be held, may be shaped like a wand, and/or may be ergometric. The handpiece or housing may allow for angular movements of the head or rotational movements of the head to make it easier for the user to access an area of the tooth.

The laser handpiece of the preferred embodiment includes a body portion 96 and a tip portion 98. The body portion 96 and tip portion 98 are connected by screw threads or other suitable coupling devices so as to allow the tip portion 98 to be detached from the body portion 96. The tip portion 98 thus may be removed and exchanged with other tip portions 98 so as to allow for the production of two or more distinctly different spot sizes, each of which corresponds to a different tip.

Figure 2A:
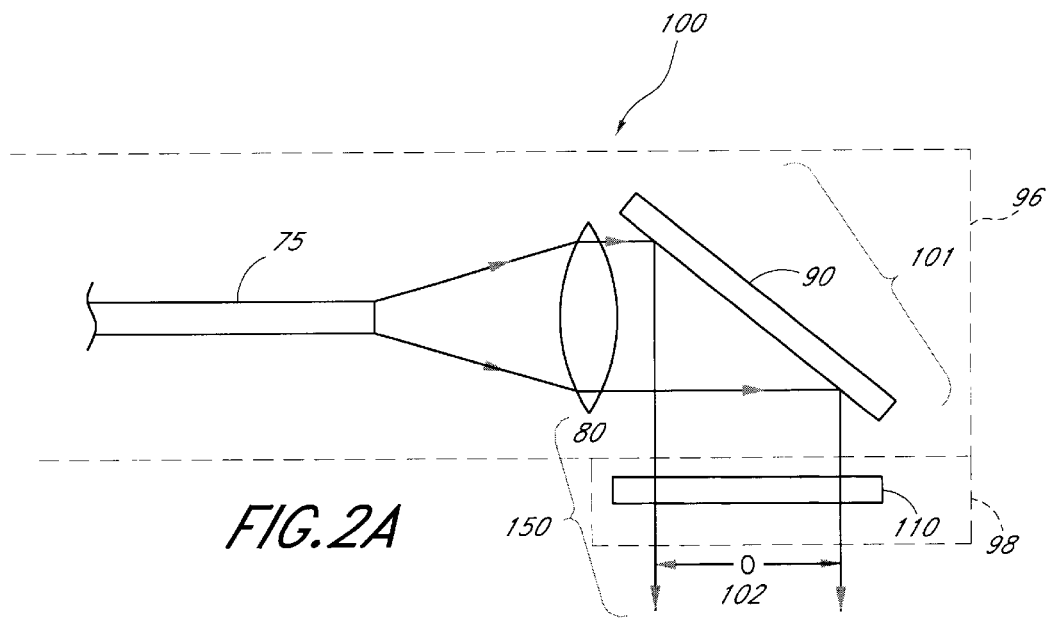
FIGS. 2A and B are side views of an embodiment of the laser handpiece in which exchangeable tips provide collimated and focused beams.
Figure 2B:
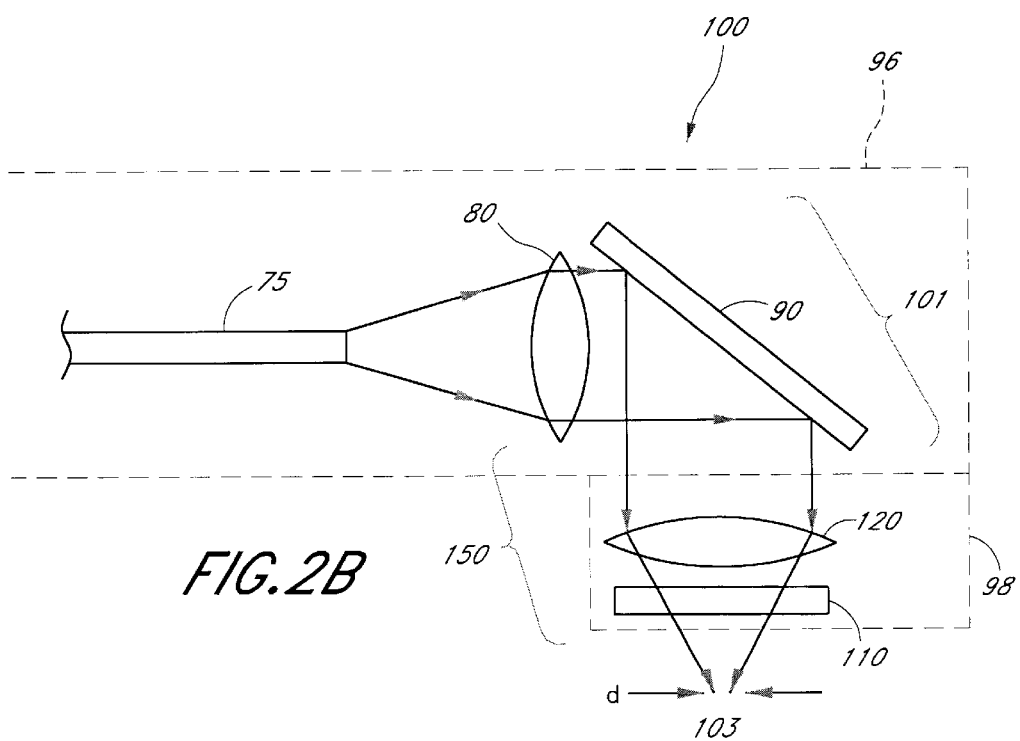
In FIG. 2B the diameter of the resulting beam is 0.2 mm.

FIGS. 2A and 2B show an internal optical assembly 101 of the laser handpiece 100. The optical assembly 101 receives light from the optical fiber 75 and redirects the light in a direction transverse to the longitudinal axis of the handpiece 100. Preferably, the optical assembly 101 is disposed at the distal end of the handpiece housing (represented by dashed lines in FIGS. 2A and 2B).

The optical assembly 101 of the laser handpiece comprises a collimating lens 80 which collimates the light exiting the fiber optic 75. The collimated light is reflected by a turning mirror 90 which redirects the light by approximately 90°. Although the preferred mirror 90 is disposed at 45° relative to the longitudinal axis of the handpiece 100, it is envisioned that the turning mirror 90 may be disposed at other angles that would transversely redirect the light, including from about 30° to about 160° relative to the longitudinal axis, including 40°, 50°, 60°, 70°, 80°, 100°, 110°, 120°, 130°, 140°, and 150°. An output window 110 is positioned to protect the inside of the handpiece from back splatter. The device shown in FIG. 2B differs from that shown in FIG. 2A in that the optical assembly 101 includes a focusing lens 120 disposed between the mirror 90 and the output window 110. This focusing lens 120 focuses the light output from the handpiece to a small spot having a diameter "d" 103. No such focusing lens is present in the device of FIG. 2A, and thus, the diameter "D" 102 of the resulting beam is relatively large. The larger diameter 102 is sized to cover relatively large surfaces, such as the lingual (back) and buccal (front) surfaces of the tooth. The diameter "d" 103 of the smaller beam is sized to cover relatively small and/or uneven surfaces, such as the occlusal (top) and unexposed surfaces (between the teeth, between the teeth and gums, etc). of the tooth.

Figure 5A:
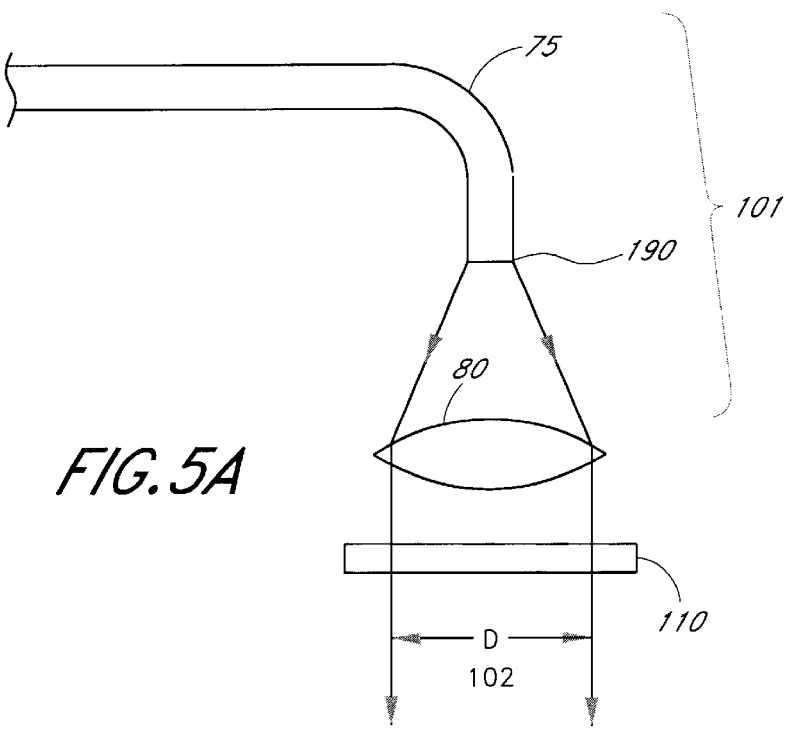
FIGS. 5A and B are side views of an embodiment of the laser handpiece in which the beam is directed by bending the fiber.
Figure 5B:
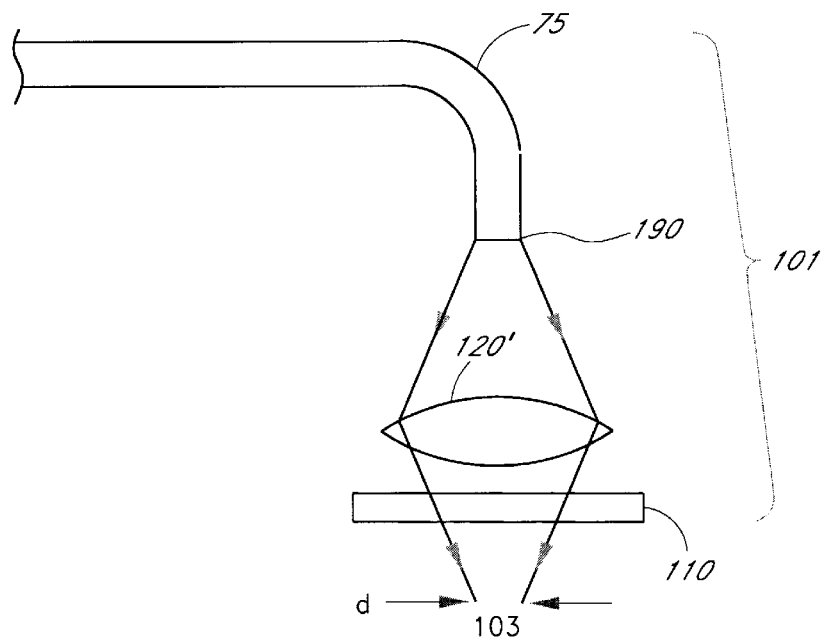
In FIG. 5B the diameter of the resulting beam is narrow.

In the preferred embodiment, a portion of the optical assembly 101, namely, the collimating lens 80 and the reflecting mirror 90 are disposed within the body portion 96 of the handpiece, while the remaining optics are disposed in the tip portion 98 of the handpiece. In the case of the tip portion 98 shown in FIG. 2A, the remaining optics 150 comprise only the window 110, and in the case of FIG. 2B, such optics 150 comprise both the window 110 and the focusing lens 120. Thus, when the tip of FIG. 5A is in place, the spot size of the output beam will be relatively large, and when the tip of FIG. 5B is in place, the output beam will have a relatively small spot size. Accordingly, it will be appreciated that, by exchanging tip portions, the handpiece may be adapted to produce either a relatively large spot size or a relatively small spot size.

In some circumstances, it may be advantageous to locate the reflecting mirror 90 in the tip portion, leaving only the collimating lens 80 in the body portion of the handpiece 100. This would allow the handpiece 100 to be adapted to output light at various angles relative to its longitudinal axis simply by exchanging tip portions, each of which has a mirror 90 disposed at a different angle that corresponds to the desired output angle.

In another embodiment, the entire optical assembly 101 is disposed in the tip portion 98. As shown in FIGS. 3A and 3B, a screw or leur connection 190 (or other suitable coupling) may allow the removal of the tip 98 with spot size "D" 102 and the attachment of the alternative tip with spot size "d" 103. Conversely, the tip 98 with spot size "d" may be exchanged with the tip 98 of spot size "D" 103. In one embodiment, the tip 98 or body 96 may be autoclavable. In a further embodiment, the body 96 may be autoclavable and the tip 98 disposable.

Figure 4:
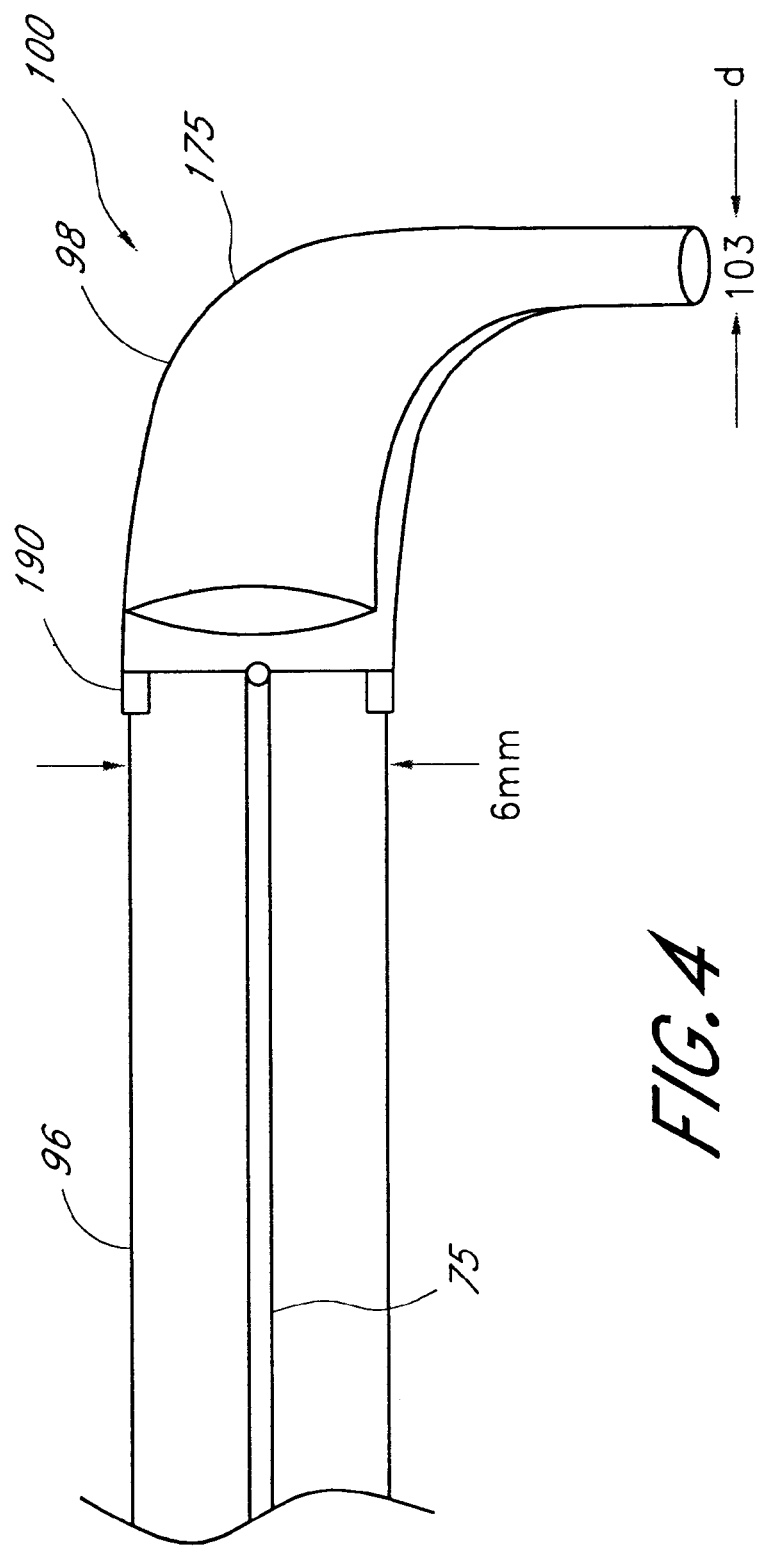
FIG. 4 is a side view of an embodiment of the laser handpiece in which the beam is directed using a mirrored metal tubing. In this figure, the diameter of the resulting beam is narrow.

A further embodiment of the small spot size tip 98 is shown in FIG. 4. The tip 98 of FIG. 4 is comprised of a light waveguide 175 which is bent to the correct angle and is tapered to produce the desired spot size diameter "d" 103. The waveguide may be a tapered glass or quartz fiber bundle, a glass tapered fiber, or a tapered metal tubing. Preferably, the metal tubing has highly reflective interior walls. By way of example, the tip 98 may be removed from or attached to the body portion 96 using the screw or leur lock 190. Other spot sizes may be provided by varying the taper angle or providing no taper at all.

In the embodiments shown in FIGS. 2–4, the turning of the beam was accomplished using either a turning mirror 90 or an optical glass waveguide 175 or a hollow tube of metal. However, the turning may be accomplished using any method known to one of skill in the art. For example, in FIGS. 5A and 5B, the turning of the beam is accomplished by bending the optical fiber 75. To produce the large spot size 102, light from the fiber 75 is transmitted through the collimating lens 80 and then through the window 110, as shown in FIG. 5A. To produce the small spot size 103, light from the fiber is transmitted through a focusing lens 120' and then through the window 110, as shown in FIG. 5B. The lens 120' differs from the lens 120 in that it receives a diverging beam rather than a collimated beam, and thus, requires different refractive properties to produce a focused output beam. Preferably, the lens (80 or 120') and window 110 are disposed in the removable tip portion 98 so as to permit varying the spot size by exchange of tips.

The diameters "D" or "d" are measured herein 1 inch from the end of the tip 98 in a direction parallel to the output beam. However, it is to be understood that since the spot size "D" is collimated one can be as close or far away as one prefers. Although, closer is much easier. However, the larger diameter spot size "D" 102 may be from about 6 to about 10 mm from the tip, preferably about 8 mm, including 6.5, 7, 7.5, 8.5, 9, and 9.5 mm. The smaller diameter spot size "d" 103 may be from about 0.1 mm to about 0.9 mm from the tip, preferably 0.2 mm, but including 0.15 mm, 0.25, 0.3, 0.35, 0.4, 0.45, 0.5, 0.55, 0.6, 0.65, 0.7, 0.75, 0.8, and 0.85 mm.

The handpiece 100 housing may be manufactured of any material which is strong, lightweight, and allows for attachment and detachment of the tips 98. In some embodiments, the body 96, the tip 98, or the whole handpiece 100 may be sterilizable. The sterilization may be accomplished using any method known to one of skill in the art. A removable portion, such as the tip 98 or all of the handpiece 100 may be autoclavable. Alternatively, the tips 98 may be disposable. Alternatively, the tips may be produced with a disposable cover.

The method of treating teeth with a laser will now be described with reference to the following Examples which are presented to describe the preferred embodiment, not to narrow the method.

EXAMPLES

The following provide examples of methods for using the laser handpiece of the preferred embodiment to treat a tooth with or without fluoride at home or in a professional setting.

Example 1

Treatment of all Surfaces of the Tooth

The dental professional applies fluoride at a concentration of about 200 ppm Fl of stannous fluoride or 1000 ppm Fl or sodium fluoride. Coherent light from an argon laser is applied to the tooth at 250 to 300 mW for 10 seconds (or longer) at an 8 mm diameter spot size on each of the surfaces. When occlusal and unexposed surfaces are treated the diameter is reduced to 5 mm, preferably by using a tip which produces a smaller spot size. This allows all of the surfaces of the tooth to be treated. Maintenance treatment includes using a fluoride mouthwash containing low concentrations of fluoride once a day, and fluoride patches containing low concentrations of fluoride applied weekly. The teeth are laser treated every 2 to 5 years. The patient may also use a fluoride toothpaste having a low concentration of fluoride. Alternatively, the fluoride composition may be any mouthwash, toothpaste, gel, restorative material, paste, patch, etc. that uses existing or lower concentrations of fluoride.

Example 2

Method of Treating a Tooth Using an Argon Laser or a Visible LED

Light from an argon laser or LED is applied to the tooth at 250 mW for 0.2 to 10 seconds at a 5 mm to 8 mm diameter spot size on all of the tooth surfaces. Preferably, the treatment lasts from 1 to 10 seconds. The teeth may also be treated with fluoride before and/or after lasing. Maintenance treatment is as in Example 1.

Example 3

Method of Treating a Tooth Using a Laser Handpiece of the Preferred Embodiment A laser handpiece configured as described in FIG. 2 is used to lase a patient's teeth in a dental office. The tip with spot diameter of 8 mm was attached and the teeth were lased, concentrating on the buccal and lingual surfaces. Then, the tip of 1 to 4 mm spot size is used at about 0.2 mm from the tooth, concentrating on the occlusal and unexposed surfaces, including the subgingival surfaces, the interproximal surfaces and the contact surfaces. Each surface is exposed to the laser for 1 to 10 seconds.

Example 4

Apparatus and Fluoride Kit for Home Use

In example 4, the fluoride and laser handpiece of the preferred embodiment are sold as a home kit. A laser handpiece configured in accordance with FIGS. 2A and B is provided with a fluoride paste to be added before treatment and a fluoride mouthwash and toothpaste. Instructions are included which state how to apply the fluoride solutions and how long to lase the teeth. The instructions also explain when each tip is used during the process and provide safety instructions. A fluoride patch may also be included in the kit.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of treating a living tooth in a mammal's mouth, comprising:
    irradiating the unexposed and occlusal surfaces of said tooth with light having a wavelength in the range of between from about 400 nm to about 810 nm, and an energy and an energy density sufficient to vaporize water and organic material without damaging the pulp of the tooth, wherein said energy density is between about 5 J/cm$^2$ to about 65 J/cm$^2$.

2. The method of claim 1, wherein said treatment heats the localized sites to a temperature of no more than about 250° C.

3. The method of claim 1, wherein said treatment heats the localized sites to a temperature of no more than about 200° C.

4. The method of claim 1, wherein said treatment heats the localized sites to a temperature of no more than about 100° C.

5. The method of claim 1, wherein said treatment heats the localized sites to a temperature of no more than about 50° C.

6. The method of claim 1, wherein the unexposed surfaces comprises the subgingival, interproximal, and contact areas of the tooth.

7. The method of claim 1, wherein the vaporization of organic material and water occurs from 3 microns to 50 microns beneath the surface of the tooth.

8. The method of claim 1, wherein the energy density is between about 5 J/cm$^2$ to 30 J/cm$^2$.

9. The method of claim 1, wherein the energy density is between about 5 J/cm$^2$ to 12 J/cm$^2$.

10. The method of claim 1, further comprising bonding a chemical agent to the crystalline structures of the tooth after removal of an organic compound.

11. The method of claim 10, wherein said chemical agent is fluoride.

12. The method of claim 11, wherein the fluoride is provided in a concentration of less than or equal to 200 ppm of stannous fluoride (0.08%) or 1000 ppm of sodium fluoride (0.275%).

13. The method of claim 11, wherein said fluoride acts by binding to hydroxide groups within the hydroxyapatite crystal.

14. The method of claim 10, wherein the chemical agent is applied as a restorative agent selected from the group consisting of: a toothpaste, a mouthwash, a gel, a paste, and a patch.

15. The method of claim 1, wherein said light comprises a coherent light source.

16. The method of claim 15, wherein said coherent light source is a laser.

17. The method of claim 16, wherein said laser is an argon laser.

18. The method of claim 17, wherein the argon laser beam is applied at 250 mW.

19. The method of claim 17, wherein the laser is applied for 10 seconds for each treated surface.

20. The method of claim 16, wherein said laser comprises a diode laser.

21. The method of claim 1, wherein said light comprises a noncoherent light source.

22. The method of claim 21, wherein said noncoherent light source is an LED.

23. The method of claim 1, wherein said tooth is treated for a period of time of more than 1 sec for each treated surface.

24. The method of claim 1, further comprising applying a chemical composition to one or more surfaces of a tooth, wherein said composition is provided as a toothpaste.

25. The method of claim 24, wherein said composition is provided as a gel.

26. The method of claim 24, wherein said composition is provided as a restorative material.

* * * * *